(12) United States Patent
Paulus et al.

(10) Patent No.: US 9,880,115 B2
(45) Date of Patent: Jan. 30, 2018

(54) METHOD FOR CHARACTERIZING A MATERIAL

(75) Inventors: Caroline Paulus, Grenoble (FR); Joachim Tabary, Grenoble (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 955 days.

(21) Appl. No.: 14/352,910

(22) PCT Filed: Oct. 21, 2011

(86) PCT No.: PCT/FR2011/000568
§ 371 (c)(1),
(2), (4) Date: May 23, 2014

(87) PCT Pub. No.: WO2013/057381
PCT Pub. Date: Apr. 25, 2013

(65) Prior Publication Data
US 2014/0286478 A1 Sep. 25, 2014

(51) Int. Cl.
*G01N 23/00* (2006.01)
*G01N 23/20* (2006.01)
*G01N 23/203* (2006.01)

(52) U.S. Cl.
CPC ........... *G01N 23/20* (2013.01); *G01N 23/203* (2013.01)

(58) Field of Classification Search
CPC .............................. G01N 23/20; G01N 23/203
See application file for complete search history.

(56) References Cited

U.S. PATENT DOCUMENTS

| 6,459,764 | B1 | 10/2002 | Chalmers et al. |
| 7,561,666 | B2 | 7/2009 | Annis |
| 2009/0052621 | A1* | 2/2009 | Walter ................. A61B 5/4869 378/53 |
| 2011/0161062 | A1 | 6/2011 | Paulus et al. |
| 2012/0123697 | A1 | 5/2012 | Fabiani et al. |

FOREIGN PATENT DOCUMENTS

| WO | 2011 009833 | 1/2011 |
| WO | 2011 069748 | 6/2011 |

OTHER PUBLICATIONS

Lalleman, A.S., et al., "A Dual X-Ray Backscatter System for Detecting Explosives: Image and Discrimination of a Suspicious Content", IEEE Nuclear Science Symposium Conference Record, pp. 299-304, (2011) XP 032117513.
International Search Report Issued May 23, 2012 in PCT/FR11/000568 Filed Oct. 21, 2011.

* cited by examiner

*Primary Examiner* — Dani Fox
(74) *Attorney, Agent, or Firm* — Oblon, McClelland, Maier & Neustadt, L.L.P.

(57) ABSTRACT

A method for characterizing a material, comprising: arranging a piece of the material near a source of ionizing photons and a detector; irradiating the piece with photons and acquiring, via the detector, two energy spectra of a photon flux that has been diffused into the material at various depths, the ratio of the photon paths in the material before and after diffusion remaining constant; determining a combined attenuation function with the spectra and the paths; selecting a plurality of energy ranges from said function; calculating, in each range, a quantity that is representative of the function; and estimating, from at least two of said quantities, a physical characteristic of the material by comparison with the same quantities obtained from known materials.

11 Claims, 7 Drawing Sheets

METHOD FOR CHARACTERIZING A MATERIAL

FIELD OF THE INVENTION

The present invention relates to a non-destructive method for characterizing a material and particularly applies to materials consisting of light chemical elements.

STATE OF THE RELATED ART

Devices for characterizing materials make use of the absorption of X-radiation transmitted through the objects to be examined, in order to identify the constituent materials thereof. These devices are however unsuitable for bulky or dense objects.

Further devices are based on backscatter. This technology only requires access to a single side of the suspect object to be inspected. In this case, the X-ray photon source and the detector are situated on the same side of the object. The X-ray photons scatter in the object rather than passing therethrough.

This technique becomes a good inspection tool for the detection and identification of materials wherein the constituent atoms have low atomic numbers, for example less than 10. These materials consist of carbon, oxygen, hydrogen, nitrogen, or fluorine. In this case, the Compton scattering phenomenon is predominant in relation to the photoelectric effect absorption phenomenon at the energies conventionally used, between approximately 50 and 200 keV.

The method described in the patent application WO 2011/009833, considered by the applicant to be close prior art, is a first approach for identifying materials using non-destructive measurements, by producing a spectrum of the backscattered radiation. This method enables an estimation of the density of the material, based on estimations of a coefficient $\mu'(E)$, called combined attenuation coefficient, at different energies. This method is also suitable for determining the ratio Zeff/A, Zeff being a quantity characterizing the material studied, called effective atomic number and A being described as the normalized molar mass of the material. The present patent application relates to an alternative to the method described in this prior patent application.

DESCRIPTION OF THE INVENTION

The aim of the present invention is that of providing a method for characterizing a constituent material of an object, this material being a pure substance or a mixture of pure substances, and a device for characterizing the material, this method and this device has having the above limitations and problems.

As a general rule, the invention is suitable for the detection and identification of material wherein the atoms have low atomic numbers, for example less than 10. It relates for example to materials consisting of carbon, oxygen, hydrogen, nitrogen or fluorine.

One aim of the invention is that of providing a reliable method for characterizing objects comprising light elements and for example organic materials.

This characterization may be performed regardless of the nature of the object and the position of the materials in the object.

A further aim of the invention is that of providing a method to be able to readily distinguish water in relation to other liquids comprising for example organic materials.

To achieve this aim, the present invention proposes to use the spectral signature scattered by an object, irradiated by an incident ionizing photon beam, this spectral signature being output by a detector.

More specifically, the invention is a method for characterizing a material comprising the following steps:

a) arranging an object made of the material to be characterized, a collimated ionizing photon source having a collimation axis and a collimated detector having a collimation axis, such that the two collimation axes are secant in the material of the object and define a scatter depth in the material of the object and a scatter angle different to zero, b) irradiating the object with ionizing photons generated by the source and acquiring, by means of the detector, a first energy spectrum corresponding to scatter of a first ionizing photon flux at a first scatter depth according to said scatter angle and a second energy spectrum corresponding to scatter of a second ionizing photon flux at a second scatter depth according to said scatter angle, the ionizing photons passing through the material by paths before and after scattering such that the ratio of the paths before and after scattering, called asymmetry factor, is substantially constant from one acquisition to another, c) determining a combined linear attenuation function based on the two energy spectra after scattering and the path difference travelled by the ionizing photons before and after scattering from one acquisition to another, d) selecting in this combined linear attenuation function a plurality of energy ranges, e) calculating in each energy range a representative quantity of the combined linear attenuation function, f) estimating on the basis of at least two of these quantities, at least one physical characteristic of the material to be characterized, by means of a comparison with the same quantities obtained using known materials.

This comparison may be carried out using an existing relation between the same quantities of known materials, called standard materials, and the known physical characteristic of said standard materials, this relation being suitable for being established experimentally, by calculation or by simulation.

Advantageously, to be specific, in step e), the representative quantity of the combined linear attenuation function is a statistical indicator such as a mean or an integral.

For the purposes of simplification, the asymmetry factor may be substantially equal to one.

During the selection of the two energy ranges, one so-called lower range comprises at least one energy less than those of the other so-called upper range, the physical characteristic of the material to be characterized estimated in step f) then being the atomic number thereof or the mass effective atomic number thereof according to whether the material to be characterized is a pure substance or a mixture.

It is preferable that in step f), a ratio between said two quantities is produced.

The lower range is advantageously between approximately 20 and 50 keV and the upper range between approximately 50 and 150 keV.

Furthermore, in step d), it is possible to select a third energy range, that comprising at least one energy greater than those of the lower range, in step f) the characteristic of the material to be characterized then being the density thereof.

Advantageously, the third energy range is between approximately 50 and 150 keV.

When, in step f), at least two physical characteristics of the material to be characterized are estimated, the method may further comprise a step for identifying the material to be characterized consisting of:
- obtaining for known materials of interest, the same physical characteristics,
- comparing the physical characteristics of the material to be characterized with those of the known materials of interest, the material being the material of interest most suitable for the comparison.

The comparison is preferably performed according to a geometric proximity criterion or a probabilistic criterion.

The present invention also relates to a device for characterizing a material comprising:
- a collimated ionizing photon source having a collimation axis, for irradiating an object of the material to be characterized with incident ionizing photons,
- a collimated detector having a collimation axis, the source and the detector being collimated such that the collimation axes thereof form a scatter angle different to zero, and are secant in the material to be characterized at a scatter depth, the detector comprising means suitable for producing an energy spectrum of an ionizing photon flux detected thereby,
- means for moving the source and/or the detector and/or the object such that the intersection of the collimation axes of the source and the detector can vary between two different scatter depths in the material to be characterized,
- means for determining a combined linear attenuation function based on a first energy spectrum corresponding to scatter of a first ionizing photon flux at a first scatter depth according to said scatter angle and a second energy spectrum corresponding to scatter of a second ionizing photon flux at a second scatter depth according to said scatter angle, and based on the positions of the source and the detector in relation to the material to be characterized, these first and second scattered ionizing photon fluxes being detected by the detector,
- means for selecting in this combined linear attenuation function a plurality of energy ranges,
- means for calculating in each energy range a representative quantity of the combined linear attenuation function,
- means for estimating on the basis of at least two of these quantities, at least one physical characteristic of the material to be characterized, by means of a comparison with the same quantities obtained using known materials.

BRIEF DESCRIPTION OF THE FIGURES

The present invention will be understood more clearly on reading the description of the merely indicative and in no way limiting examples of embodiments given, with reference to the appended figures wherein.

Identical, similar or equivalent parts of the various figures described hereinafter bear the same reference numbers for easier transition from one figure to another.

The various parts represented in the figures are not necessarily represented on a uniform scale, to render the figures easier to read.

DETAILED DESCRIPTION OF PARTICULAR EMBODIMENTS

Figure 1:
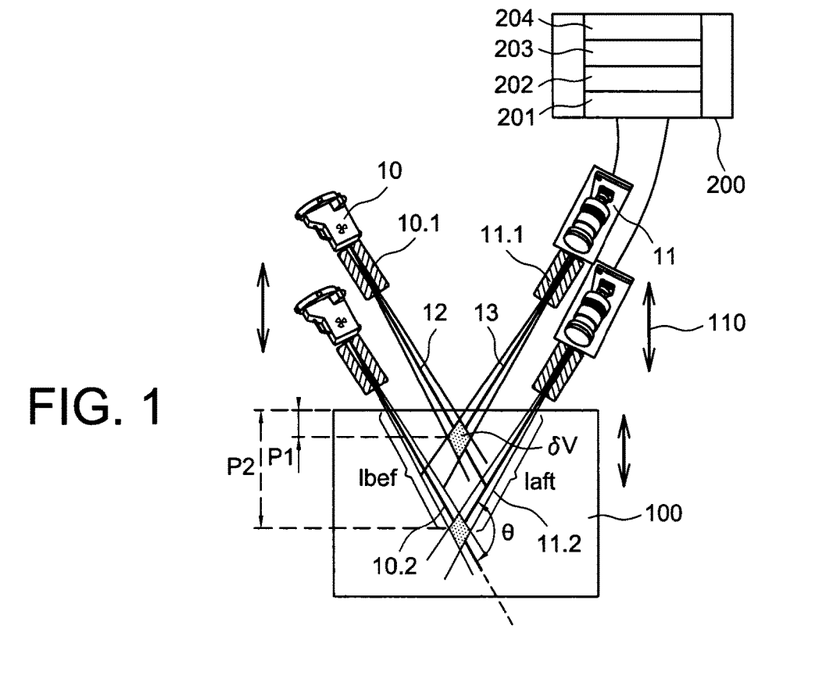
FIG. 1 represents a device for characterizing a material according to the invention.
Figure 2:
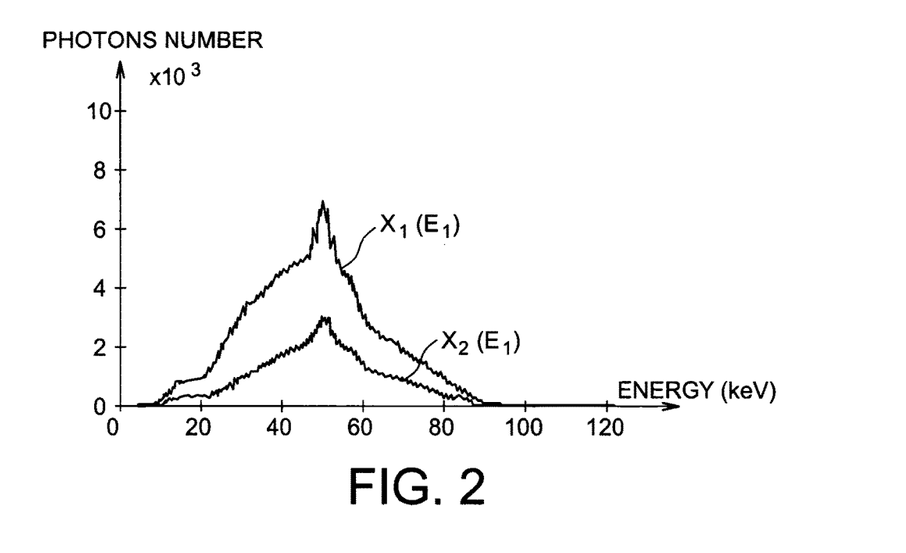
FIG. 2 illustrates the energy spectrum of the scattered ionizing photon flux acquired by the spectrometric detectors during measurements, the scatter volume being situated at two different depths in the object.

Reference will be made to FIGS. 1 and 2 respectively showing a device for implementing the method according to the invention and a representation of spectra obtained during the use of the device.

The device comprises an ionizing photon source 10 and an advantageously spectrometric detector 11. It is assumed that the energies used are those typically output by X or gamma ionizing photons, and that they are typically between a few keV and approximately 300 keV. It is also assumed that, in the example described, at least one object 100 made of material to be characterized is used and that this object 100 consists of a single material, this material being a pure substance or a mixture of pure substances. It has been represented as a substantially rectangular block. Other shapes may obviously be used provided that the shape and the position of the surface of the object in relation to the source and the detector are known.

The ionizing photon source 10 and spectrometric detector 11 are collimated and each have a central collimation axis and the collimation angle is generally small, preferentially less than approximately 10° and more particularly less than 5° C. The collimator of the ionizing photon source 10 is referenced 10.1 and the collimator of the spectrometric detector 11 is referenced 11.1. The central collimation axes are referenced 10.2 and 11.2 in FIG. 1. The ionizing photon source 10 is polychromatic, for example an X-ray generating tube. A plurality of isotopic sources could also be used. The intensity of the ionizing radiation produced by the X-ray generating tubes being greater than that of the radiation production by isotopic sources, X-ray generating tubes are preferred.

The ionizing photon source 10 is intended to produce an incident ionizing photon beam 12 wherein the spectrum is a function of the energy $E_0$.

The incident ionizing photon beam 12 penetrates the material of the object 100, at a substantially plane zone, and scatters in an inspection volume $\delta V$, situated at a given scatter depth. Attenuation occurs between the emission by the ionizing photon source 10 and the inspection volume $\delta V$. A scattered ionizing photon beam 13 is generated and it is detected by the spectrometric detector 11. Attenuation occurs between the inspection volume $\delta V$ and the spectrometric detector 11. These incident and scattered ionizing photon beams each have a central axis. The central axis of the incident ionizing photon beam 12 corresponds to the central collimation axis 10.2 of the source 10. Similarly, the central axis of the scattered and detected ionizing photon beam 13 corresponds to the central collimation axis 11.2 of the detector 11.

The inspection volume $\delta V$ corresponds to the intersection between the incident ionizing photon beam 12 and the scattered ionizing photon beam 13 to the spectrometric detector 11. Due to the collimation of the ionizing photon source 10 and the spectrometric detector 11, the incident and scattered ionizing photon beams are defined spatially, and the intersection thereof in the material to be characterized of the object 100 defines an inspection volume $\delta V$. This inspection volume $\delta V$ is relatively small, typically in the region of one cubic centimeter. The collimation angles of the ionizing photon source 10 and the spectrometric detector 11 will be chosen accordingly. The incident ionizing photon beam 12 and the detected scattered ionizing photon beam 13 are separated by a scatter angle $\theta$, as illustrated in FIG. 1. This scatter angle $\theta$ is the angle between the central axis of the incident ionizing ray beam 12 and the central axis of the detected ionizing ray beam 13, this scatter angle being zero if there is no scatter. The inspection volume $\delta V$ extends around the intersection, in the object 100, of the central collimation axes of the ionizing photon source 10 and the spectrometric detector 11.

The object 100 will be irradiated with the incident ionizing photon beam 12 so as to obtain an inspection volume $\delta V$ at a given scatter depth in the material of the object 100 and, using the spectrometric detector 11, the scattered ionizing photon flux will be acquired, the spectrometric detector 11 thus performs acquisitions of the scattered ionizing photon flux. This scattered ionizing photon flux, annotated X(E1), corresponds to the number of ionizing photons reaching the sensitive surface of the spectrometric detector 11. As seen hereinafter, at least two consecutive acquisitions of the scattered ionizing photon flux are made. For this, the ionizing photon source 10, the spectrometric detector 11 and the object 100 are moved in relation to each other, such that scattering occurs at different scatter depths in the material of the object. Means for moving the source and/or the detector and/or the object in relation to each other have been represented with the reference 110. The two positions are illustrated in FIG. 1, the scatter depths, measured from the surface of the object 100 whereby the incident ionizing photon beam 12 enters the object 100 are referenced P1 and P2, respectively. The positioning of the ionizing photon source 10 and the spectrometric detector 11 from one acquisition to another will be performed by keeping the same scatter angle $\theta$. The ionizing photon source 10 and the spectrometric detector 11 may be moved, for example, along a substantially perpendicular direction to the surface of the object to be characterized, this surface being assumed to be substantially plane at least locally.

The device for characterizing the material further comprises means 200 for processing the two energy spectra output by the spectrometric detector 11. They will be described in more detail hereinafter.

By limiting itself to the first Compton scatter, the incident ionizing photon beam 12 at the energy $E_0$ emitted by the ionizing photon source 10 is subject to three interaction processes before reaching the spectrometric detector 11. The first is an attenuation in the material to be characterized before scatter in the inspection volume, the second is the scatter, the third being an attenuation in the material to be characterized after scatter.

When performing the two acquisitions, it is ensured that the ratio between the lengths of the paths travelled by the ionizing photons in the material to be characterized before scatter and after scatter remain substantially constant from one acquisition to another. The term $l_{bef}$ refers to the length of the path travelled by the ionizing photons in the material to be characterized before scatter. The term $l_{aft}$ refers to the length of the path travelled by the ionizing photons in the material to be characterized after scatter. The term asymmetry factor $\epsilon$ denotes the ratio $l_{bef}/l_{aft}$. It could equally well have been possible to study another asymmetry factor $\epsilon'$ corresponding to the ratio $l_{aft}/l_{bef}$ and thus equalling $1/\epsilon$. The ionizing photon source 10, the spectrometric detector 11 and the sample 100, are positioned during both acquisitions, such that the asymmetry factor $\epsilon$ remains substantially constant.

The ionizing photon flux X(E1) scattered in the inspection volume $\delta V$ and having reached the sensitive front face of the spectrometric detector may be expressed with the formula (1), it is then assumed that the material is a mixture of pure substances:

$$X(E_1) = \Phi(E_0) \cdot e^{-\mu(E_0, Z) \cdot l_{bef}} \left[ \frac{d\sigma_{KN}(E_0, \theta)}{d\Omega} \delta\omega \frac{N_a \cdot S(E_0, \theta, Z_{eff-a}) \cdot \rho}{A_{norm}} \cdot \delta V \right] e^{-\mu(E_1, Z) \cdot l_{aft}}. \quad (1)$$

wherein:

$\Phi(E_0)$ is the fluence rate of the ionizing photons produced by the source:

$$E_1 = \frac{E_0}{1 + \alpha(1 - \cos\theta)}$$

is the scattered energy of the ionizing photons detected by the spectrometric detector after scatter according to the scatter angle $\theta$, where $\alpha = E_0/m_e c^2$, $m_e$ being the mass of the electron at rest, or $9.1093097 \times 10^{-31}$ kg and c the speed of light in a vacuum or 299792458 m/s, the ionizing photons of the incident ionizing photon beam 12 before scatter having the energy $E_0$;

$\mu(E_0,Z)$ and $\mu(E_1,Z)$ are linear attenuation functions of the material before and after scatter at the respective energies $E_0$ and $E_1$;

$$\frac{d\sigma_{KN}(E_0, \theta)}{d\Omega}$$

is the Compton electron effective scattering cross-section given by the Klein-Nishina formula;

$\delta\omega$ is the solid angle whereby the spectrometric detector is viewed from each point of the inspection volume $\delta V$, this solid angle is not illustrated so as not to congest FIG. 1;

$N_a$ is Avogadro's number;

$A_{norm}$ is the normalized molar mass of the material to be characterized and is defined by $$A_{norm} = \sum_i \alpha_i^{at} A_i$$

$\alpha_i^{at}$ are the atomic percentages of each constituent chemical element of the material to be characterized, each $\alpha_i^{at}$ is defined on the basis of the mass percentage $\omega_i$ and the atomic mass $A_i$ of the chemical element i:

$$\alpha_i^{at} = \frac{\frac{\omega_i}{A_i}}{\sum_{i=1}^{n} \frac{\omega_i}{A_i}};$$

$Z_{eff-a}$ is the effective atomic number of the material to be characterized, this material being a mixture, it is of the same type as the atomic number for a pure substance. It is expressed by $$Z_{eff-a} = \sum_{i=1}^{n} \alpha_i^{at} Z_i;$$

$s(E_0, \theta, Z_{eff-a})$ is an incoherent scatter function, it tends towards $Z_{eff-a}$ when $E_0$ increases;

$\rho$ is the density of the material to be characterized.

Hereinafter in the application, the quantity $Z_{eff-m}$ corresponding to the mass effective atomic number of the material to be characterized, this material being a mixture, will also be used. It is of the same type as the atomic number for a pure substance. It is expressed by $$Z_{eff-m} = \sum_{i=1}^{n} \omega_i Z_i,$$

$\omega_i$ is the mass percentage of the atom i in the material.

If the material to be characterized is a pure substance, formula (1) will comprise instead of $Z_{eff-a}$ and $A_{norm}$ respectively Z and A, i.e. the atomic number and the molar mass of the pure substance. In this case, $Z_{eff-m}$ is also equal to Z.

During an acquisition with a given inspection volume, at a given scatter depth, the spectrometric detector thus outputs a signal $X(E_1)$ which is the energy spectrum of the scattered flux in the inspected volume $\delta V$ according to the scatter angle $\theta$. The detector 11 comprises means 11.3 for outputting such energy spectra. FIG. 2 illustrates the energy spectrum of the ionizing photon flux having scattered in the inspection volume $\delta V$ and having reached the sensitive front face of the spectrometric detector, for two positions of the inspection volume at different scatter depths P1, P2 in the material to be characterized, retaining a constant scatter angle $\theta$ in both positions. This flux corresponds to the number of ionizing photons having a given energy detected by the spectrometric detector. The ionizing photon flux reaching the sensitive front face of the spectrometric detector when the scatter volume is at the scatter depth P1 is called the first ionizing photon flux and annotated $X_1(E_1)$ and the ionizing photon flux reaching the sensitive front face of the spectrometric detector when the scatter volume is at the scatter depth P2 is called the second ionizing photon flux and annotated $X_2(E_1)$.

By compiling in formula (1) all the independent terms of the material into a single coefficient annotated k(E1), formula (1) is simplified, becoming formula (1'):

$$X(E_1) = k(E_1) \cdot \frac{\rho \cdot S(E_0, \theta, Z_{eff-a})}{A_{norm}} e^{-\mu'(E_1, \varepsilon) l_{aft}} \quad (1')$$

Combined linear attenuation function denotes the term $\mu'(E_1, \epsilon)$ hereinafter expressed as $\mu'(E_1)$. It is the sum of the linear attenuation function at the incident energy $E_0$ before scatter and the linear attenuation function at the scattered energy $E_1$ after scatter, one of the attenuation functions being weighted by an asymmetry factor. When the weighting affects the linear attenuation function at the incident energy $E_0$, the asymmetry factor $\epsilon$ is used and when the weighting affects the linear attenuation function at the scattered energy $E_1$, the asymmetry factor $\epsilon'$ is used. In the example described, the combined linear attenuation function is expressed by formula (2):

$$\mu'(E_1) = \mu(E_1, Z) + \epsilon \cdot \mu(E_0, z) \quad (2)$$

It is then possible to calculate directly the combined linear attenuation function $\mu'(E_1)$ which is expressed by formula (3):

$$\mu'(E_1) = \frac{1}{l_{aft2} - l_{aft1}} \ln\left(\frac{X_1(E_1)}{X_2(E_1)}\right) = \frac{1}{\Delta l} \ln\left(\frac{X_1(E_1)}{X_2(E_1)}\right) \quad (3)$$

$l_{aft1}$ and $l_{aft2}$ are the lengths of the path travelled by the ionizing photons in the material to be characterized, after scatter, for one of the acquisitions, or for the other acquisition. The term $\Delta l$ is called the path difference. When the asymmetry factor is such that $\epsilon = l_{bef}/l_{aft}$ then $\Delta l = l_{aft2} - l_{aft1}$.

In the case whether the asymmetry factor is defined by $\epsilon' = l_{aft}/l_{bef}$, it can be demonstrated that:

$$\mu'(E_1) = \frac{1}{l_{bef2} - l_{bef1}} \ln\left(\frac{X_1(E_1)}{X_2(E_1)}\right) = \frac{1}{\Delta l} \ln\left(\frac{X_1(E_1)}{X_2(E_1)}\right) \quad (3')$$

where $\mu'(E_1) = \epsilon' \cdot \mu(E_1, Z) + \mu(E_0, Z)$

The path difference $\Delta l$ is then such that $\Delta l = l_{bef2} - l_{bef1}$, $l_{bef1}$ and $l_{bef2}$ are the lengths of the path travelled by the ionizing photons in the material to be characterized before scatter for one of the acquisitions, or for the other acquisition.

Hereinafter in the description, it is considered that $\epsilon = l_{bef}/l_{aft}$.

For these two acquisitions, the movement of the ionizing photon source 10, the spectrometric detector 11 in relation to the object 100 is known and also the path difference $\Delta l$, $\Delta l = l_{aft2} - l_{aft1}$.

The inventors observed that the behaviour of the combined linear attenuation function $\mu'(E_1)$ as a function of the scattered energy $E_1$ was very similar to that of the linear attenuation function $\mu(E_1)$ as a function of the energy $E_1$. In any case, there is a bijection between $\mu'(E_1)$ and $\mu(E_1)$.

Figure 3:
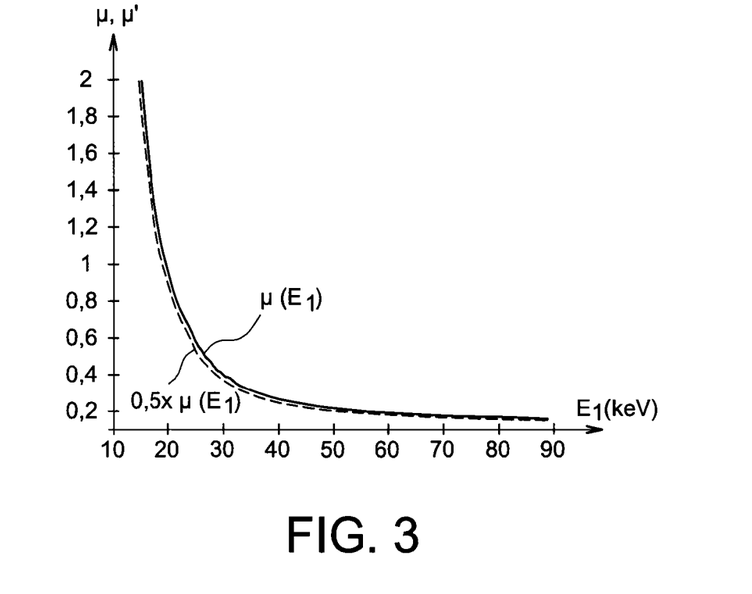
FIG. 3 illustrates, on the same graph, the linear attenuation function and the combined linear attenuation function as a function of the scattered energy weighted by a factor of 0.5, this figure was obtained by calculation accounting for a backscatter angle of 120°.

Reference may be made to FIG. 3 showing the variation of the combined linear attenuation function $\mu'(E_1)$, weighted by a factor of 0.5, and the linear attenuation function $\mu(E_1)$ as a function of the scattered energy $E_1$ in a case where the scatter angle $\theta$ equals 120°. In this particular case studied, $\epsilon$ is equal to one and $\mu(E_1)$ approximates $0.5 \cdot \mu'(E_1)$.

The variation of the combined linear attenuation function $\mu'(E_1)$ is such that for high energies, the curve has a horizontal asymptote and, for low energies, a vertical asymptote.

If it is possible to extract at least one physical characterised of the material to be characterized based on the linear attenuation function $\mu(E_1)$, it is possible to extract the same physical characteristic of the combined linear attenuation function $\mu'(E_1)$.

It can be expressed in general that:

$\mu(E) = \rho \mu(E)/\rho$ where $\rho$ is the density in g·cm$^{-3}$ of the material. Therefore, also, $\mu(E) = \rho \sigma(E)$ where $\sigma(E)$ is the mass attenuation function of the material in cm$^2$/g. These two quantities $\rho$ and $\sigma(E)$ are suitable for characterizing the material.

The composite materials which are mixtures of pure substances, the mass attenuation function is equal to:

$$\sigma(E) = \sum_i \omega_i \sigma_i(E)$$

where $w_i$ is the mass proportion of each pure substance in the mixture and $\sigma_i(E)$ is the mass attenuation function of each pure substance in the mixture, these quantities are known and tabulated.

In the same way as a combined linear attenuation function $\mu'(E)$ is defined above, it is possible to define a combine mass attenuation function $\sigma'(E)$ where $\sigma'(E) = \mu'(E)/\rho$.

Figure 4:
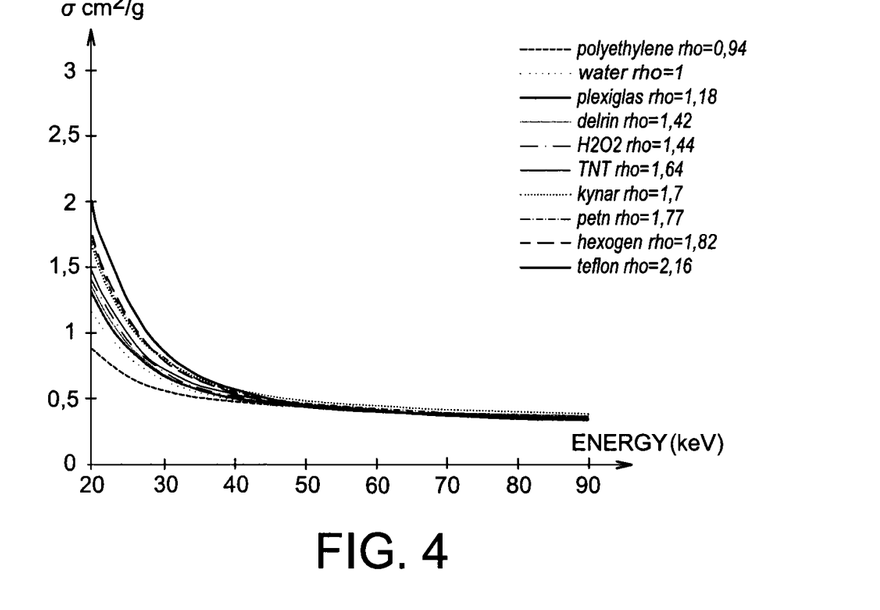
FIGS. 4 and 5 show the variations of the combined mass attenuation function $\sigma'(E)$ as a function of the scattered energy $E_1$, the variation of the combined linear attenuation function $\mu'(E)$ as a function of the scattered energy $E_1$ for a number of routine materials, these figures were obtained by calculation accounting for a backscatter angle of 120°.
Figure 5:
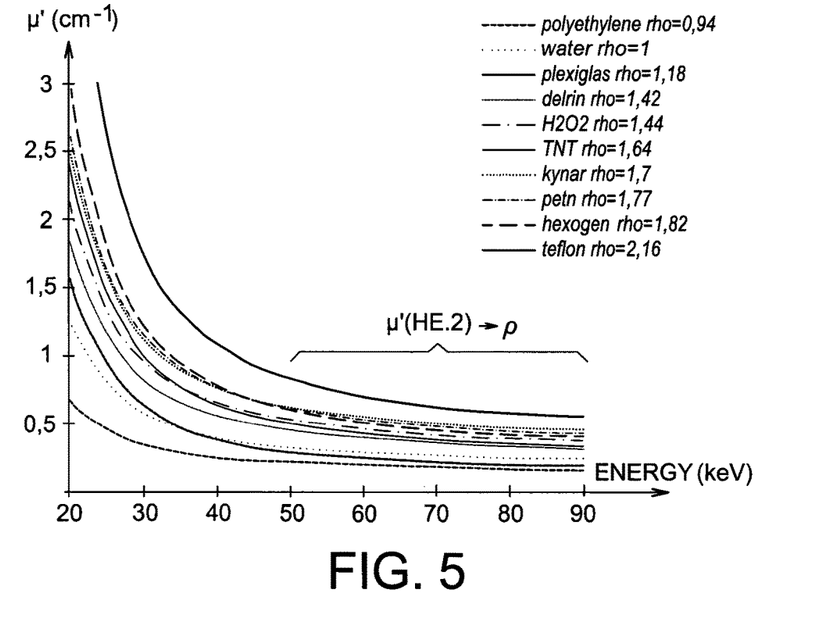

FIGS. 4 and 5 represent firstly the variation of the combined mass attenuation function $\sigma'(E)$ as a function of the scattered energy E and the variation of the combined linear attenuation function $\mu'(E)$ as a function of scattered E for a number of routine materials. It is seen that, in these two figures, the progression of the curves is similar within the factor $\rho$.

The mass attenuation function $\sigma(E)$ has a high-energy predominant Compton component, this component conveying the ability of the material to scatter the incident ionizing photons with a change of wavelength and a low-energy predominant photoelectric component, this photoelectric component conveying the ability of the material to stop the incident ionizing photons.

In this context, the term low energy denotes an energy less than approximately 50 keV, the term high energy denotes an energy greater than or equal to approximately 50 keV. For routine materials in a mixture, consisting of light pure elements such as hydrogen, carbon, oxygen, nitrogen, they may comprise a greater proportion of oxygen and nitrogen than hydrogen or carbon. However, these predominant pure elements are the heaviest. The atomic number Z is equal to 7 for nitrogen, 8 for oxygen whereas it is merely equal to 6 for carbon and 1 for hydrogen. One consequence of this is that these materials have a high mass effective atomic number, between approximately 6.7 and 8. A further consequence is that the slope of decline of the curve illustrating the variation of the combined linear attenuation function $\mu'(E)$ as a function of E is greater than that which the combined linear attenuation function would have had for other materials with a lower mass effective atomic number. The latter observation stems from the fact that, at low energies, the predominant effect is the photoelectric effect for which the mass attenuation function $\sigma(E)$ is proportional to $Z^r/E^s$ where the exponent r is between approximately 3.1 and 4 and the exponent s is substantially equal to 3.

Figure 6:
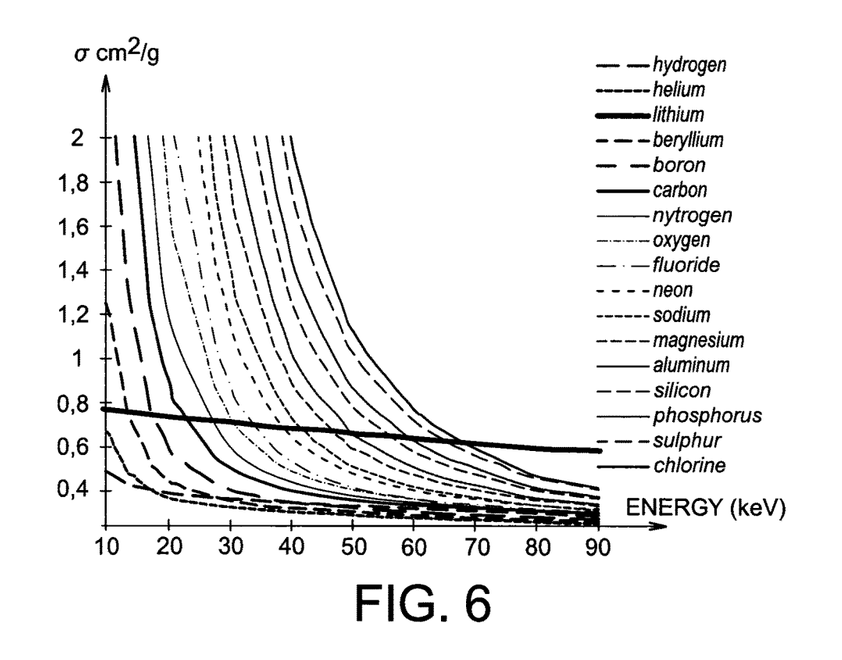
FIG. 6 shows the variation of the mass attenuation function as a function of the energy for a number of pure substances.

With reference to FIG. 6, illustrating the variation of the mass attenuation function $\sigma(E)$ as a function of the energy for a range of pure substances, it is observed that the slope, at a given energy, of oxygen and nitrogen is greater than that of hydrogen or carbon, for energies less than 50 keV.

The same conclusion may be drawn for, on one hand, materials consisting of pure substances and, on the other, the combined mass attenuation function $\sigma'(E)$.

Figure 7:
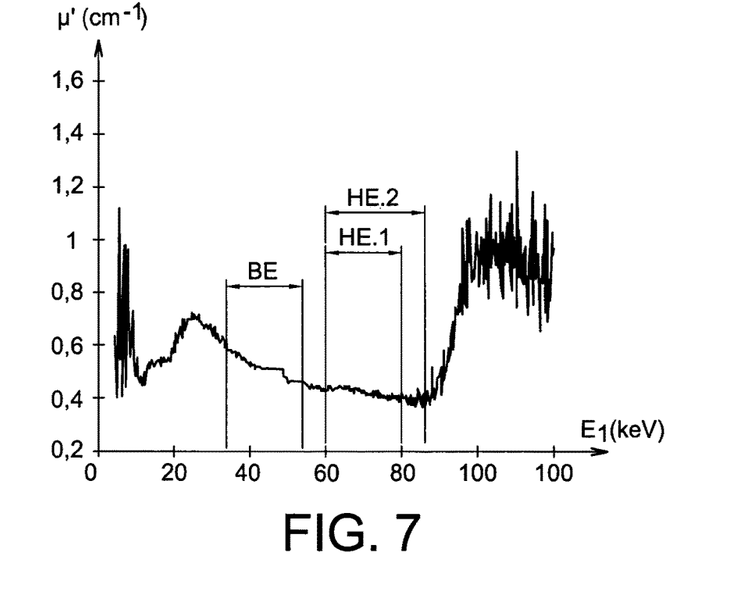
FIG. 7 shows the selection of the energy ranges in the representation of the combined linear attenuation function as a function of the scattered energy.

To obtain access to the slope and subsequently the atomic number or the mass effective atomic number depending on whether the material to be identified is a pure substance or not, the inventors recommend selecting at least two separate energy ranges in the representation of the combined linear function $\mu'(E_1)$ as a function of the scattered energy $E_1$, one extending in lower energies than the other. These two low energy ranges may overlap, meaning that they are not necessarily separated. The lower energy range is called BE in FIG. 7 and the higher range is called HE.1. This FIG. 7 illustrates the variation of the combined linear attenuation function $\mu'(E_1)$ as a function of the scattered energy $E_1$.

By calculating for each energy range BE and HE.1, a representative quantity $\eta$ of the combined linear attenuation function $\mu'(E_1)$, at least one physical characteristic of the material to be characterized will be deduced therefrom. The representative quantity $\eta$ of the combined linear attenuation function $\mu'(E_1)$ is preferably a statistical indicator. In the example discussed and illustrated using FIG. 7, the representative quantity $\eta$ of the combined linear attenuation function $\mu'(E_1)$ is a mean of said function. The arithmetic mean will generally be adopted, although other types of mean may be envisaged such as the geometric mean, the harmonic mean. Alternatively, instead of calculating a mean, an integral could be calculated, wherein the bounds are those of the range. Further statistical indicators are possible such as the median for example. The mean of the combined linear attenuation function over the range BE is called $\mu'_{mean}(BE)$ and the mean of the combined linear attenuation function over the range HE.1 is called $\mu'_{mean}(HE.1)$. These two means will be used by comparing same, for example by determining the ratio thereof, to estimate the atomic number Z or the mass effective atomic number $Z_{eff-m}$ of the material to be characterized. An advantage of using a ratio of the two means of the combined linear attenuation function is that the density $\rho$ has been removed.

Figure 8:
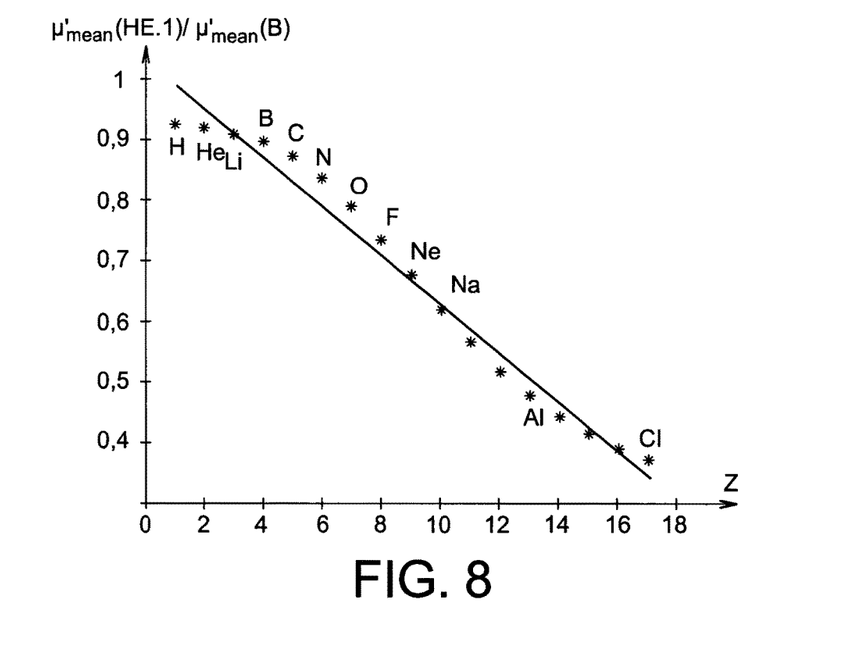
FIGS. 8 and 9 show the existing relation, for pure substances or mixtures, respectively, between the atomic number Z thereof or the mass effective atomic number $Z_{\mathit{eff\text{-}m}}$ thereof and the value of the ratio $\mu'_{mean}$ (HE.1)/$\mu'_{mean}$ (BE)

FIG. 8 is a graph clearly showing the relationship, for standard pure substances, between the atomic number Z thereof and the value of the ratio $\mu'_{mean}(HE.1)/\mu'_{mean}(BE)$. The mean of the combined linear attenuation function over the range BE $\mu'_{mean}(BE)$ and the mean of the combined linear attenuation function over the range HE.1 for standard materials were obtained by calculation.

The higher the atomic number Z, the lower the ratio $\mu'_{mean}(HE.1)/\mu'_{mean}(BE)$. The range BE is between 35 and 45 keV and the range HE.1 is between 50 and 75 keV. The asterisks correspond to standard pure substances.

The line passing through the largest number of asterisks makes it possible to demonstrate the relationship existing between the ratio $\mu'_{mean}(HE.1)/\mu'_{mean}(BE)$ and Z over a wide range of Z values.

After calculating the ratio $\mu'_{mean}(HE.1)/\mu'_{mean}(BE)$ for the material to be characterized that is assumed to be a pure substance, by noting same in the graph on the y-axis, the atomic number thereof is readily estimated, on the x-axis, using the line.

Figure 9:
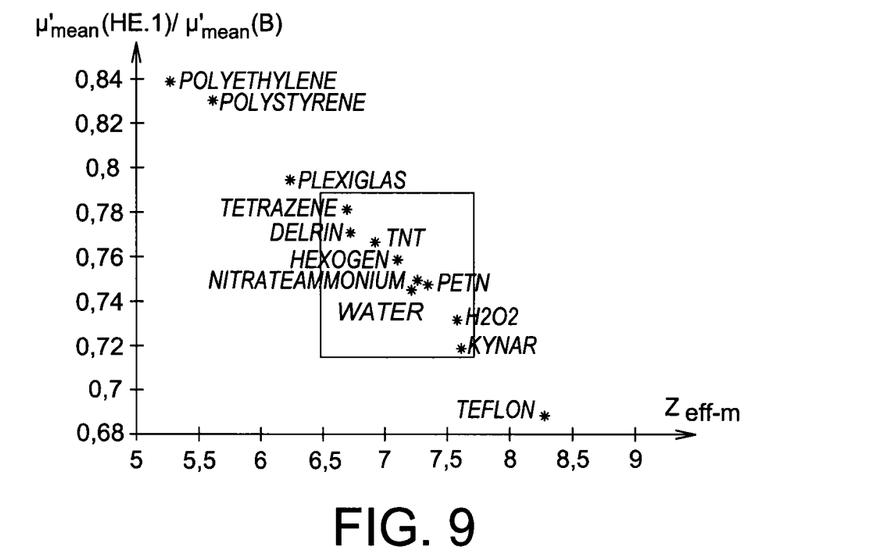

The description given above for pure substances also applies for standard materials which are mixtures of pure substances. FIG. 9 illustrates the relationship existing between the ratio $\mu'_{mean}(HE.1)/\mu'_{mean}(BE)$ and the mass effective atomic number $Z_{eff-m}$ of routine materials, these materials containing oxygen, carbon, hydrogen or nitrogen. In practical terms, based on standard materials for which the relationship between the mass effective atomic number and the ratio $\mu'_{mean}(HE.1)/\mu'_{mean}(BE)$ is tabulated, it is easy to determine the mass effective atomic number $Z_{eff-m}$ of the material to be characterized. In this FIG. 9, three groups of materials in a mixture have been defined, those containing carbon, hydrogen, oxygen having a low mass effective atomic number less than 6.5, those containing carbon, hydrogen, oxygen, nitrogen having a high mass effective atomic number between 6.5 and 7.5 or even 8 and those containing heavier materials for example fluorine, chlorine, having an mass effective atomic number greater than 8.

Furthermore, for routine materials consisting of light pure elements such as hydrogen, carbon, oxygen, nitrogen, fluorine, etc., it is observed that the combined mass attenuation function $\sigma'(E)$ converges to the same value, once high energies are attained, for example greater than several tens of keV, for which Compton scattering is predominant. In this way, the combined linear attenuation function $\mu'(E)$ tends, for high energies, towards a value which is only essentially dependent on the density $\rho$ of the material.

According to the invention, a third energy range HE.2 is selected, for which the Compton effect is predominant, a representative quantity $\eta'$ of the combined linear attenuation function $\mu'(E)$ on this third range is calculated and, by means of this quantity $\eta'$, the density $\rho$ of the material to be characterized is estimated. The energy range HE.2 is a range corresponding to high energies, for example, between 50 keV and 150 keV. This is represented schematically in FIG. 7. The range HE.2 has at least one energy higher than those of the range BE. In this way, the range BE and the range HE.2 may partially overlap. The ranges HE.1 and HE.2 may be merged, may partially overlap or be separate.

As explained above, the representative quantity $\eta'$ of the combined linear attenuation function $\mu'(E)$ may be a statistical indicator such as a mean or an integral of said combined linear attenuation function $\mu'(E)$, calculated on the range HE.2. In practical terms, based on the tabulated density data for various routine standard materials and on the quantity $\eta'$ in the third energy range HE.2, it is easy to demonstrate a relationship between the quantity $\eta'$ and the density $\rho$. The quantity $\eta'$ for standard materials is obtained under the same conditions for spectrum acquisition, calculating and selecting the energy range as the quantity $\eta'$ for the material to be characterized.

Figure 10:
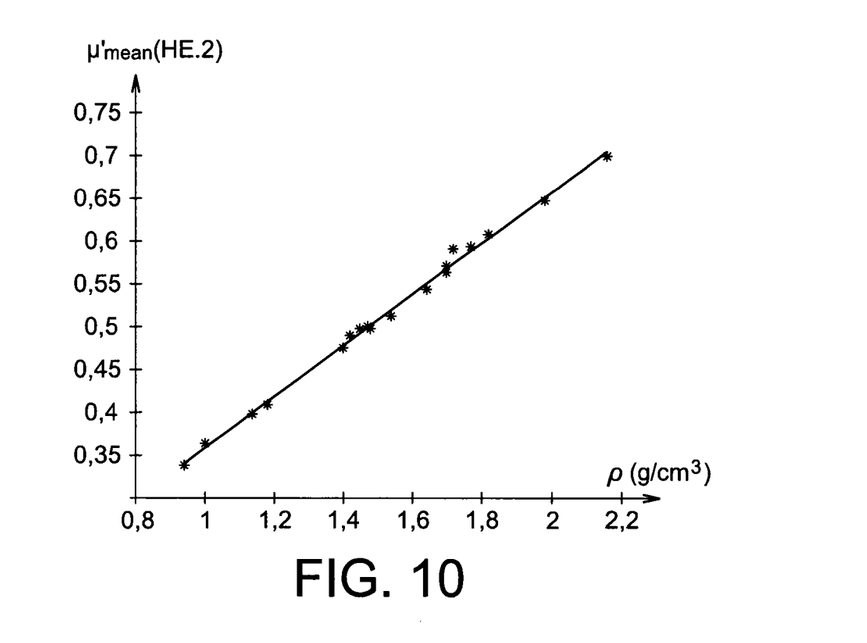
FIG. 10 shows the existing relation, for routine standard materials, between $\mu'_{mean}$ (HE.2) and the density thereof.

FIG. 10 shows the relationship between the density $\rho$ of various routine standard materials and the mean $\mu'_{mean}$(HE.2) of the combined linear attenuation $\mu'(E)$ on the energy range HE.2. Each point corresponds to a standard material. It is assumed that, in the example in FIG. 10, the energy range HE.2 is from 50 keV to 100 keV. The line passing through the greatest number of points makes it possible to demonstrate the relationship existing between $\mu'_{mean}$(HE.2) and $\rho$, over a wide range of values of $\rho$ between 0.8 and 2.2 g/cm$^3$.

The three energy ranges BE, HE.1, HE.2 are to be optimized according to the materials to be characterized and according to the energies that the spectrometric detector is capable of detecting with a satisfactory energy resolution.

Following the previous steps, a set of physical characteristics are thus available for the material to be characterized, i.e. in the example described, the density thereof and the atomic number thereof or the mass effective atomic number thereof. This set is hereinafter referred to at the estimated set of physical characteristics.

With the above, the processing means 200 of the characterizing device according to the invention, illustrated in FIG. 1, thus comprise means 201 for determining a combined linear attenuation function based on the two energy spectra detected by the detector, corresponding to two scatter depths of the intersection of the collimation axes of the source and the detector and the position of the source and the detector in relation to the object. In fact, as seen above, the path difference LP travelled by the ionizing photons before or after scatter from one acquisition to another is used.

They also comprise:
  means 202 for selecting in this combined linear attenuation function a plurality of energy ranges,
  means 203 for calculating in each energy range a representative quantity of the combined linear attenuation function,
  means 204 for estimating on the basis of at least two of these quantities, at least one physical characteristic of the material to be characterized, by means of a comparison with the same quantities, obtained with known materials.

An existing relationship between the same quantities of standard materials and the known physical characteristics of said standard materials is used, these quantities of standard materials being suitable for being obtained using the device by replacing the object made of the material to be characterized by samples of standard materials. These quantities of standard materials may also be estimated by means of calculations or modelling.

The method according to the invention may further comprise a step for identifying the material to be characterized with a comparison, according to a defined criterion, between the estimated set of physical characteristics with sets of the same physical characteristics of known materials of interest, hereinafter referred to as sets of known physical characteristics. These physical characteristics of known materials are also known, they are found in publications, encyclopaedias, literature of manufacturers marketing these materials and on the Internet.

For this, there may be, in a multi-dimensional space, on one hand, a plurality of sets of known physical characteristics, and, on the other, the estimated set of physical characteristics to perform the comparison according to the defined criterion. The material to be characterized is then the known material of interest most suitable for the comparison.

Figure 11:
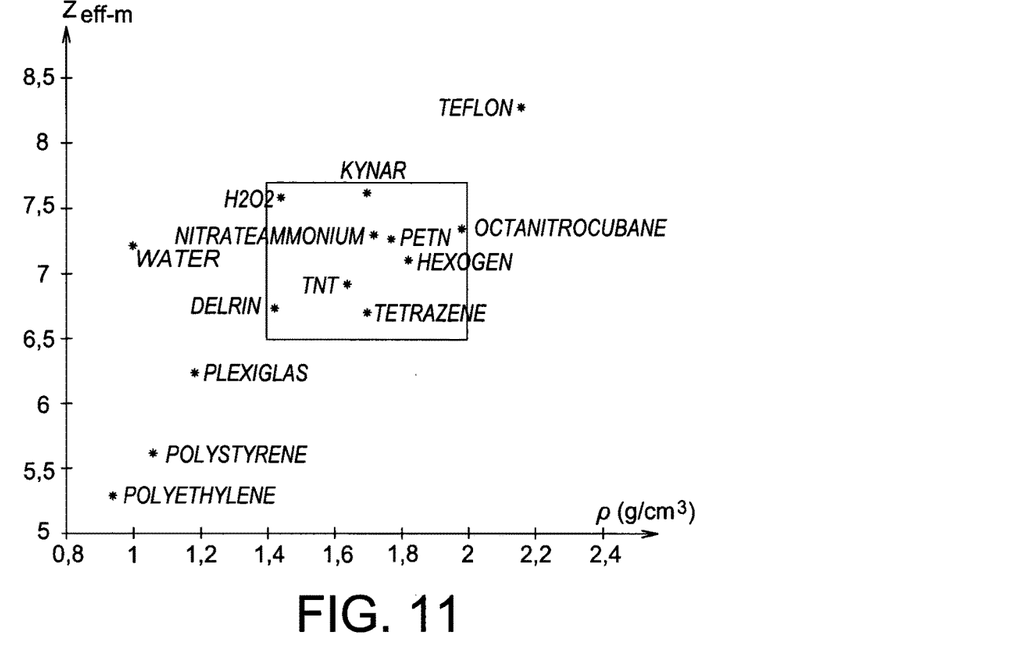
FIG. 11 shows a two-dimensional space $Z_{\mathit{eff\text{-}m}}$ ($\rho$) containing sets of pairs $Z_{\mathit{eff\text{-}m}}$/$\rho$ for known materials of interest.

FIG. 11 gives the example of a two-dimensional reference frame wherein asterisks are positioned, each corresponding to a mass effective atomic number $Z_{eff-m}$–density ρ set of a known material.

These materials are either materials considered to be hazardous, such as RDX (cyclotrimethylene trinitramine), TNT (trinitrotoluene), nitroglycerin, DNT (dinitrotoluene), tetrazene, octanitrocubane, or more common materials such as polyethylene, polystyrene, Plexiglas, polyurethane, Kynar which is a PVDF (polyvinylidene fluoride) marketed by Arkema, polytetrafluoroethylene known as the trademark Teflon registered by DuPont, a polyamide such as that known under the name of nylon which is a trademark of Burbery's, polyoxymethylene known as the trademark Delrin registered by DuPont.

It is observed that, in this reference frame, the materials considered to be hazardous are all grouped together in a boxed zone, and that the other more common materials are outside this zone.

The defined criterion may be a proximity criterion in respect of distance between the estimated set of physical characteristics and each of the sets of known physical characteristics.

With reference again to the example in FIG. 11, the estimated mass effective atomic number-density set is obtained in this reference frame. It has been represented by a dot. With the comparative criterion, the known mass effective atomic number-density set which is geometrically closest to the estimated mass effective atomic number-density set is sought in the reference frame. In the example in question, it consists of Kynar.

It is possible to use a comparative criterion other than the proximity in respect of distance. For example, it is possible to use a probabilistic comparative criterion, if the known materials make reference to probability distributions. Once the estimated set of physical characteristics is located in the space where each of the sets of known physical characteristics are situated, the material to be characterized is that which is in the vicinity of the set of known physical characteristics having the greatest probability.

The description above is based on the fact that the material to be characterized is identified using two of the physical characteristics thereof. It may be necessary in some cases to include a further physical feature in the research on the material. It will be possible for this to determine this further physical characteristic, based on at least one representative quantity η of the combined linear attenuation function μ'(E) on at least one further energy range. For the determination of a given material, it will be possible to use for one of the characteristics a statistical indicator η, for example the mean, and for a further characteristic a further statistical indicator, for example the integral.

If more than two physical characteristics are required, the identification will no longer be performed in a two-dimensional space, but in a space with more than two dimensions. The number of dimensions is dependent on the number of estimated physical characteristics.

We will now apply the method according to the invention to an actual concrete example. This example is obviously not limiting. The characterizing device used is that illustrated in FIG. 1. The object 100 analyzed is a cubic block of 0.5 dm³ of Kynar. The physical characteristics of this material are as follows: density ρ=1, 79 g/cm³, mass effective atomic number $Z_{eff-m}$=7.62. It is obviously assumed that the material of the sample 100 is unknown and that it is sought to identify same.

Figure 12:
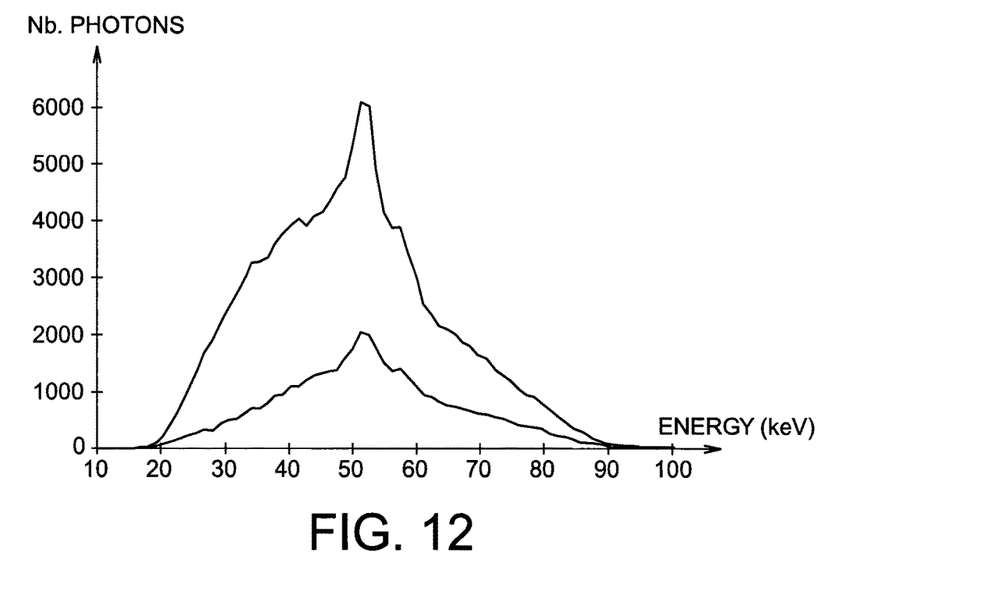
FIG. 12 represents the energy spectrum of the scattered ionizing photon flux acquired by the spectrometric detectors during experimental measurements with, as an object, a sample made of Kynar, the scatter volume being situated at two different depths in the sample.

A scatter angle θ of 120° is used. During irradiation, two acquisitions of the scattered ionizing photon flux are performed, for one acquisition, the inspection volume δV is at a scatter depth P1=15 mm from the surface whereby the incident ionizing photon beam penetrates the material to be characterized of the object. For the other acquisition, the inspection volume δV is at a scatter depth P2=30 mm from said surface. The two scattered photon flux spectra output by the spectrometric detector are illustrated in FIG. 12.

If the curve of the combined linear attenuation function μ'(E) as a function of the scattered energy E is constructed, as described above, the representation in FIG. 13 is obtained.

Figure 13:
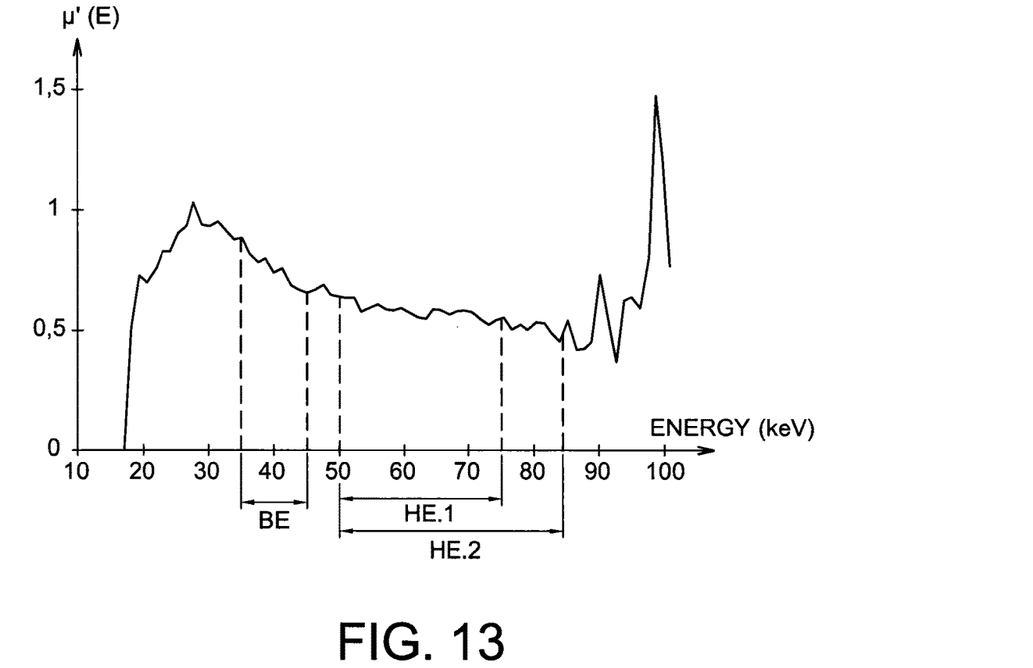
FIG. 13 illustrates, also in the experimental context of a sample made of Kynar, the relation between the combined linear attenuation function and the scattered energy.

Based on this curve, the following windows are selected: BE=35-45 keV, HE.1=50-75 keV and HE.2=50-83 keV. It is ensured that the lower range BE does not include very low energies, in this case less than 30 keV, since it is observed that the curve falls sharply. This fall is essentially due to the influence of the response of the spectrometric detector.

Based on the two windows BE and HE.1, a first physical characteristic of the material to be characterized, i.e. the mass effective atomic number $Z_{eff-m}$ thereof, is estimated. As a representative quantity η, the combined linear attenuation function μ'(E), the arithmetic mean $μ'_{mean}(E)$ of said combined linear attenuation function on the range BE and on the range HE.1 are used. The result of the calculation gives $Z_{eff-m}$=7.7628.

A second physical characteristic of the material to be characterized, the density p, is estimated. As a representative quantity η of the combined linear attenuation function μ'(E), the arithmetic mean $μ'_{mean}(E)$ of said combined linear attenuation function μ'(E) on the third range HE.2 is used. The result of the calculation gives ρ=1.7948 g/m³.

These estimations are made using standard materials as described above.

Figure 14:
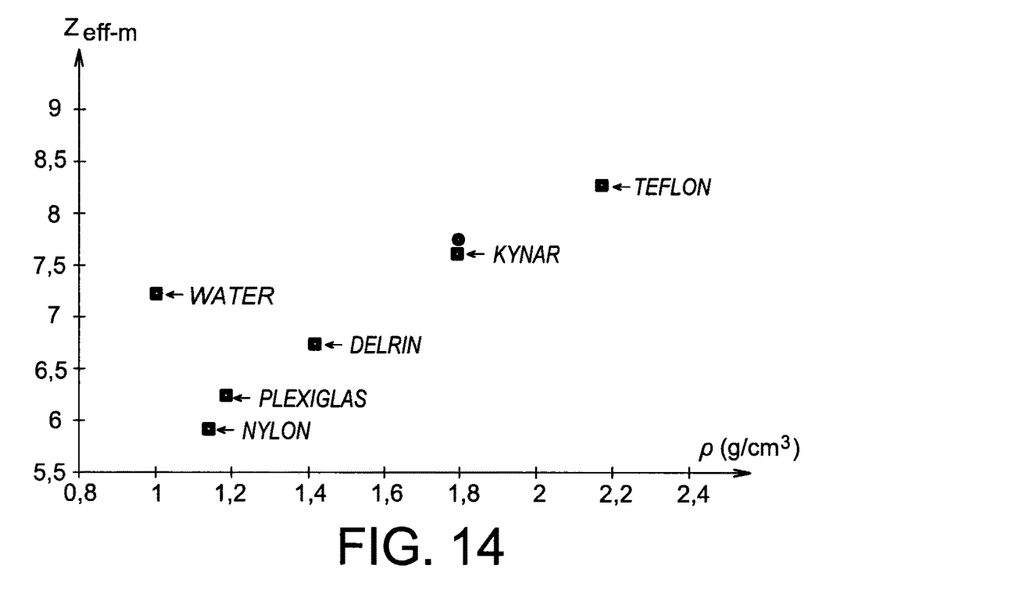
FIG. 14, also in the experimental context of a sample made of Kynar, illustrates the estimation of the density thereof and the mass effective atomic number thereof, to be compared to the equivalent known quantities of known materials of interest.

In a two-dimensional space $Z_{eff-m}(ρ)$ illustrated in FIG. 14, mass effective atomic number-density sets of known materials such as water, Teflon, Kynar, Delrin, Plexiglas, nylon are positioned. They are represented by squares. In this space, the estimated mass effective atomic number-density set of the material to be characterized is positioned, this set is represented by the black circle. The mass estimated effective atomic number-density set is compared to those of known materials. The black circle is geometrically closest to the square for Kynar, indicating that the material to be characterized is probably Kynar.

The invention claimed is:

1. Method for characterizing a material comprising the following steps:
   a) arranging an object made of the material to be characterized, a collimated ionizing photon source having a collimation axis and a collimated detector having a collimation axis, such that the two collimation axes are secant in the material of the object and define a scatter depth in the material of the object and a scatter angle different to zero,
   b) irradiating the object with ionizing photons generated by the source and acquiring, by means of the detector, a first energy spectrum corresponding to scatter of a first ionizing photon flux at a first scatter depth according to said scatter angle and a second energy spectrum corresponding to scatter of a second ionizing photon flux at a second scatter depth according to said scatter angle, the ionizing photons passing through the material by paths before and after scattering such that the ratio of the paths before and after scattering, called asymmetry factor, is substantially constant from one acquisition to another, c) determining a combined linear attenuation function based on the two energy spectra after scattering and the path difference travelled by the ionizing photons before and after scattering from one acquisition to another, d) selecting in this combined linear attenuation function a plurality of energy ranges, e) calculating in each energy range a representative quantity of the combined linear attenuation function, f) estimating on the basis of at least two of these quantities, at least one physical characteristic of the material to be characterized, by means of a comparison with the same quantities obtained using known materials.

2. Method according to claim 1, wherein, in step e), the representative quantity of the combined linear attenuation function is a statistical indicator such as a mean or an integral.

3. Method according to claim 1, wherein the asymmetry factor is substantially equal to one.

4. Method according to claim 1, wherein, when in step d), two energy ranges including a lower range and an upper range are selected, the lower range comprising at least one energy less than those of the upper range, the physical characteristic of the material to be characterized estimated in step f) is the atomic number thereof or the mass effective atomic number thereof.

5. Method according to claim 1, wherein, in step f), a ratio between said two quantities is produced.

6. Method according to claim 4, wherein the lower range is between approximately 20 and 50 keV and the upper range is between approximately 50 and 150 keV.

7. Method according to claim 4, wherein, when in step d), a third energy range is selected, comprising at least one energy greater than those of the lower range, in step f) the characteristic of the material to be characterized then being the density thereof.

8. Method according to claim 7, wherein the third energy range is between approximately 50 and 150 keV.

9. Method according to claim 1, wherein, when in step f), at least two physical characteristics of the material to be characterized are estimated, the method further comprises a step for identifying the material to be characterized consisting of:

obtaining for known materials of interest, the same physical characteristics, comparing the physical characteristics of the material to be characterized with those of the known materials of interest, the material being the material of interest most suitable for the comparison.

10. Method according to claim 9, wherein the comparison is performed according to a geometric proximity criterion or a probabilistic criterion.

11. Device for characterizing a material, comprising:

a collimated ionizing photon source having a collimation axis, for irradiating an object of the material to be characterized with incident ionizing photons, a collimated detector having a collimation axis, the source and the detector being collimated such that the collimation axes thereof form a scatter angle different to zero, and are secant in the material to be characterized at a scatter depth, the detector comprising means suitable for producing an energy spectrum of an ionizing photon flux detected thereby, means for moving the source and/or the detector and/or the object, such that the intersection of the collimation axes of the source and the detector can vary between two different scatter depths in the material to be characterized, means for determining a combined linear attenuation function based on a first energy spectrum corresponding to scatter of a first ionizing photon flux at a first scatter depth according to said scatter angle and a second energy spectrum corresponding to scatter of a second ionizing photon flux at a second scatter depth according to said scatter angle, and based on the positions of the source and the detector in relation to the material to be characterized, these first and second scattered ionizing photon fluxes being detected by the detector, means for selecting in this combined linear attenuation function a plurality of energy ranges, means for calculating, in each energy range, a representative quantity of the combined linear attenuation function, means for estimating on the basis of at least two of these quantities, at least one physical characteristic of the material to be characterized, by means of a comparison with the same quantities obtained using known materials.

* * * * *